(12) United States Patent
Wooddell et al.

(10) Patent No.: US 7,262,056 B2
(45) Date of Patent: Aug. 28, 2007

(54) ENHANCING INTERMOLECULAR INTEGRATION OF NUCLEIC ACIDS USING INTEGRATOR COMPLEXES

(75) Inventors: Christine Wooddell, Madison, WI (US); Hans Herweijer, Madison, WI (US); Jon A. Wolff, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 0 days.

(21) Appl. No.: 10/291,342

(22) Filed: Nov. 8, 2002

(65) Prior Publication Data

US 2004/0126887 A1  Jul. 1, 2004

Related U.S. Application Data

(60) Provisional application No. 60/344,865, filed on Nov. 8, 2001.

(51) Int. Cl.
   *C12N 15/00* (2006.01)
   *C12N 15/74* (2006.01)
   *C12N 15/861* (2006.01)
   *C12N 15/66* (2006.01)
   *C12N 1/20* (2006.01)

(52) U.S. Cl. ............... 435/455; 435/473; 435/69.1; 435/252.8; 435/91.41

(58) Field of Classification Search ............ 435/473, 435/455, 458, 183, 91.41; 530/350
See application file for complete search history.

(56) References Cited

U.S. PATENT DOCUMENTS

| 5,348,874 A | * | 9/1994 | Savakis et al. ............. 435/464 |
| 6,159,736 A | * | 12/2000 | Reznikoff et al. .......... 435/455 |
| 2002/0031502 A1 | * | 3/2002 | Raasmaja et al. ........ 424/93.21 |
| 2002/0115216 A1 | * | 8/2002 | Steer et al. ................. 435/455 |
| 2003/0143740 A1 | * | 7/2003 | Wooddell et al. ........... 435/455 |

FOREIGN PATENT DOCUMENTS

WO   WO98/10077   *   3/1998

OTHER PUBLICATIONS

Constans, Transposable Elegance, The Scientist, Mar. 2000, vol. 14:5, p. 24.*
Mirus, TransIT-LT1 transfection reagent, online protocol revised Oct. 2001.*
Gao and Huang, Potentiation of Cationic Liposome-Mediated Gene Delivery by Polycations, Biochemistry, 1996, vol. 35, pp. 1027-1036.*
Maekawa et al, A cell-free system of Tn3 transposition and transposition immunity, Genes to Cells, 1996, vol. 1, pp. 1007-1016.*

* cited by examiner

*Primary Examiner*—Joseph Woitach
*Assistant Examiner*—Maria Marvich
(74) *Attorney, Agent, or Firm*—Mark K. Johnson; Kirk Ekena

(57) ABSTRACT

We disclose compositions and processes for enhancing transposon mediated integration of a nucleic acid molecule into another target nucleic acid molecule. Integration by an integrator complex is enhanced by cationic reagents.

9 Claims, 5 Drawing Sheets pNeo-Tn:

pEGFP-Tn:

pSEAP-Tn:

pNeo/siRNA-Tn:

SEQUENCE LISTING

<160> NUMBER OF SEQ ID NOS: 4

<210> SEQ ID NO 1
<211> LENGTH: 19
<212> TYPE: DNA
<213> ORGANISM: Transposon Tn5

<400> SEQUENCE: 1
ctgactctta tacacaagt                                              19

<210> SEQ ID NO 2
<211> LENGTH: 19
<212> TYPE: DNA
<213> ORGANISM: Transposon Tn5

<400> SEQUENCE: 2
ctgtctcttg atcagatct                                              19

<210> SEQ ID NO 3
<211> LENGTH: 19
<212> TYPE: DNA
<213> ORGANISM: Transposon Tn5

<400> SEQUENCE: 3
ctgtctctta tacacatct                                              19

```
<210> SEQ ID NO 4
<211> LENGTH: 19
<212> TYPE: DNA
<213> ORGANISM: Transposon Tn5

<400> SEQUENCE: 4
agatgtgtat aagagacag                                                    19
```

ENHANCING INTERMOLECULAR INTEGRATION OF NUCLEIC ACIDS USING INTEGRATOR COMPLEXES

This application claims priority benefit of U.S. Provisional Application Ser. No. 60/344,865 filed Nov. 8, 2001.

BACKGROUND

DNA transposition is an important mechanism in the rearrangement of genomes and horizontal gene transfer in prokaryotic as well as eukaryotic cells. Transposons were initially discovered by Barbara McClintock in maize and members of the Tc1/mariner family of transposable elements have been found in organisms that range from protozoans to humans. A transposable element has short inverted repeats flanking the DNA sequence which typically encodes a transposase (or integrase in retroviruses). The transposase binds these elements to excise the transposon from one location in the DNA and insert it into another. A characteristic of integration by transposable elements is the duplication of a short segment of genomic sequence flanking the insertion sites. After the transposon has inserted into the target site, host enzymes duplicate the target site sequence to repair the DNA. These duplications are characteristic for each transposon: for Tn5 they are 9 bp, for murine leukemia virus 4 bp, and for the Tc1/mariner family duplications are 2 bp.

Transposition systems are well established as in vivo tools for genetics and genome analysis. Transposition in eukaryotic cells occurs naturally through retroviral infection and via Tc1/mariner type elements. Integration capabilities of retroviral vectors and adeno-associated viral vectors have been studied as candidates for gene transfer.

Cell-free systems for intermolecular transposition (for DNA sequencing, to create deletions or insertions into genes, for studying protein domain functions) have been developed from Tn5 [Goryshin and Reznikoff 1998; Epicentre, Madison, Wis.], Tn7 [Gwinn et al. 1997], Mu [Haapa et al. 1999], and the yeast Ty1 virus-like particles [Devine and Boeke 1994].

Mechanisms involved in Tn5 transposition have been carefully characterized by Reznikoff and colleagues. The transposon has two pairs of 19 bp elements that are utilized by the transposase: outer elements (OE) and inner elements (IE). After a monomer is bound to each end of the transposon, the two monomers dimerize, forming a synapse. Tn5 then transposes by a cut-and-paste mechanism. Tn5 transposes with a relaxed target site selection [Goryshin and Reznikoff 1998] and can insert into multiple locations within a single gene.

The frequency of transposition is very low for most transposons. The natural down regulation of Tn5 transposition was overcome by selection of hyperactive transposase and by optimizing the transposase-binding elements [Goryshin and Reznikoff 1998, Zhou et al. 1998]. This hyperactive transposase, combined with optimized transposon sequence elements, transposes with high efficiency [Goryshin and Reznikoff 1998, Braam et al. 1999].

SUMMARY

Figure 1:
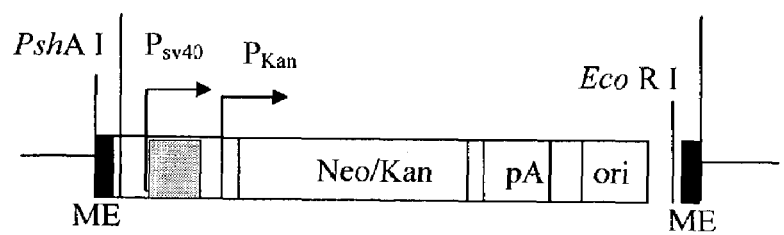
FIG. 1. The transposon components of plasmids pNeo-Tn (pMIR126), pEGFP-Tn (pMIR151), pSEAP-Tn (pMIR136), and pNeo/siRNA-Tn (pMIR246) including the 19 bp mosaic elements (ME, black boxes) are shown. The ME's are inverted repeats. The transposons of each of these plasmids include the SV40 promoter driving the neomycin resistance gene and a prokaryotic promoter to allow for kanamycin resistance in bacterial cells. In plasmids pNeo-Tn, pEGFP-Tn, and pSEAP-Tn the bacterial origin of replication is included in the transposon. In pNeo/siRNA-Tn, the bacterial origin is outside of the transposon elements. Blunt-ended transposons were released from each of the plasmids by digestion with restriction enzyme PshA I. Just internal to each of the ME's is the restriction site indicated. Prokaryotic promoter ($P_{Kan}$), eukaryotic promoters ($P_{CMV}$, $P_{SV40}$ and $P_{UbC}$), SV40 or HSV TK polyA sequences (pA), the bacterial origin of replication (ori) and the f1 origin or replication (f1 ori) are shown.
Figure 1:
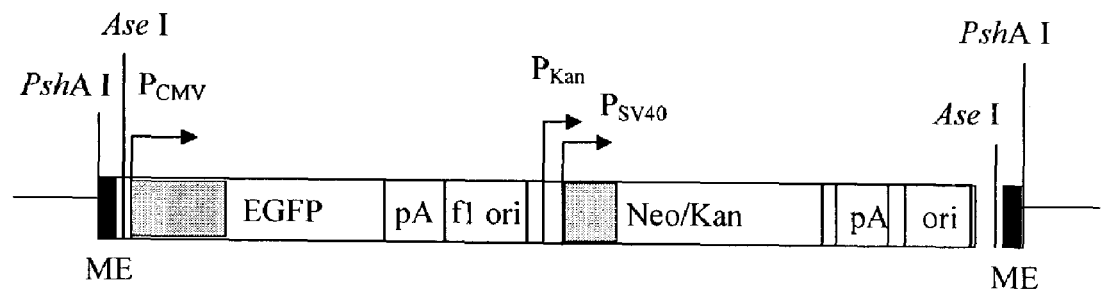
Figure 1:
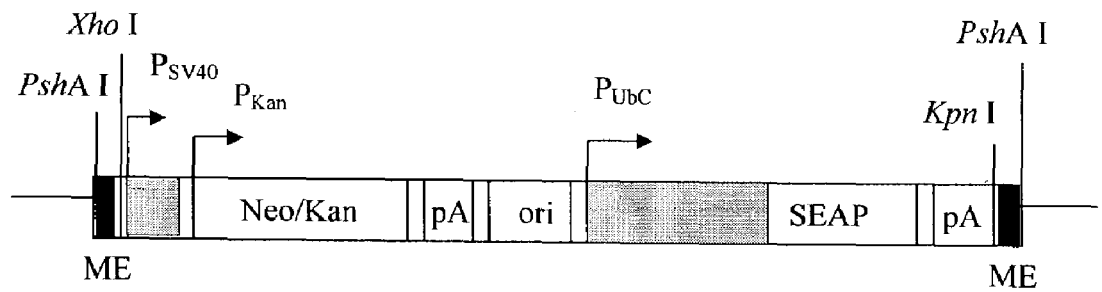
Figure 1:
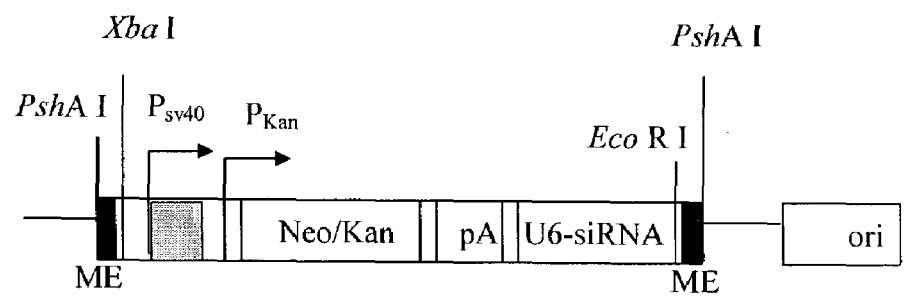

In a preferred embodiment, we describe a process for enhancing integration of a transposon into a target nucleic acid comprising: making a transposon; forming a complex between the transposon, its cognate transposase and an enhancing reagent; and integrating the transposon into a target nucleic acid. Any nucleic acid sequence of appropriate size that is flanked by appropriate elements may be integrated into a target nucleic acid using this procedure. A preferred transposon is a Tn5 transposon. A preferred Tn5 transposon is a transposon flanked by mosaic elements. A preferred transposase is a Tn5 transposase. A preferred Tn5 transposase is a hyperactive Tn5 transposase. Enhancing reagents are selected from the list comprising: transfection reagents, polycations, cationic polymers and cationic lipids. A preferred cationic polymer is polyethyleneimine.

In a preferred embodiment, compositions comprising transposase integrator complexes and enhancing reagents for the purposes of integrating a transposon into a target nucleic acid are described. The integrator complex may be formed on a transposon that is linear or circular. The transposon may comprise all or a portion of the nucleic acid in the integrator complex. A preferred transposase is a Tn5 transposase. A preferred Tn5 transposase is a hyperactive Tn5 transposase. A preferred hyperactive Tn5 transposase is the EK54/MA56/LP372 mutant Tn5 transposase. A preferred transposon is a Tn5 transposon. A preferred Tn5 transposon is a transposon flanked by mosaic elements. Enhancing reagents are selected from the list comprising: transfection reagents, polycations, cationic polymers and cationic lipids. A preferred cationic polymer is polyethyleneimine.

In a preferred embodiment, the present invention provides a process for integrating a transposon into a target nucleic acid comprising; forming an integrator complex, preparing a composition comprising mixing a transfection reagent with the integrator complex in a solution, and adding the composition to a target nucleic acid wherein the transposon is integrated into the target nucleic acid. Preferred transfection reagents include TRANSIT®-LT1, TRANSIT®-INSECTA, TRANSIT®-293 (histone+1,4-bis(3-oleoylamidopropyl) piperazine+3-[(cholamidopropyl)dimethylammonio]-1-propanesulfonate), and polyethyleneimine. Other transfections reagents that may be used include cationic polymers such as polylysine, cationic polymer conjugates, cationic proteins, liposomes, cationic lipids and combinations of these.

In a preferred embodiment, any nucleic acid sequence that is flanked on either side by appropriate sequences to which a transposase can bind may be used in the process. The nucleic acid sequence plus these flanking sequences together are called the transposon. The specific flanking sequences, or elements, depend on the transposase that is to be used to integrate the transposon into a target nucleic acid. A preferred transposon is the Tn5 transposon. A preferred flanking sequence is the 19 base pair mosaic element (ME) recognized by the Tn5 transposase. Other preferred flanking sequences are the outside Tn5 element (outside ends) and the inside Tn5 element (inside ends). The transposon may by linear or circular. The transposon may be flanked by additional sequences such as in a plasmid. The plasmid may be linear, circular or supercoiled.

In a preferred embodiment, the compositions and processes may be used to provide random insertional mutagenesis, wherein integration of a transposon into a target nucleic acid inserts a molecular tag or disrupts a target sequence. Integration into a coding region can disrupt gene function and facilitate study of a gene. Integration of molecular tags can facilitate cloning, sequencing, or identification by providing a detectable marker.

In a preferred embodiment, the compositions and processes may be used to identify enhancer elements wherein; a transposon is created with a weak promoter and a reporter gene, and the transposon is integrated into a target nucleic acid, such as a bacterial artificial chromosome (BAC) or yeast artificial chromosome (YAC). Activity of the reporter gene is then monitored in response to different experimental conditions. A reporter gene in a transposon that is integrated near an enhancer will be expressed in conditions where the enhancer is active. Insulator sequences can be included to further define the location of the enhancer relative to the transposon insertion point. An insulator sequence may be placed on either side of the reporter gene in the transposon. After transposon integration into the nucleic acid, it is then delivered to the appropriate species for the enhancer trap assay.

Another approach to enhancer trapping is to have a reporter gene with a minimal promoter on a plasmid vector. Transposons containing unknown sequence can be amplified and integrated into the reporter gene vector to determine which fragments contain enhancers. DNA of interest, up to approximately 10 kb long, can be amplified by polymerase chain reaction using primers with transposon element sequence. When the sequence of a DNA is not known, transposon insertion can be used to facilitate sequencing the region. Creating a library of randomly inserted transposons allows sequencing of large nucleic acids from many different transposon insertion positions. The use of transposons carrying drug-resistance markers facilitates selection and cloning of nucleic acid containing the transposon integration. The sequenced nucleic acid can then be made into transposons.

In a preferred embodiment, the described compositions and processes can be used to integrate large fragments of DNA with known ends into a target nucleic acid such as a plasmid, artificial chromosome or viral vector. Integration of large DNA (up to 20 kb) by an integrator complex does not require the use of restriction enzyme sites.

Further objects, features, and advantages of the invention will be apparent from the following detailed description when taken in conjunction with the accompanying drawings.

DETAILED DESCRIPTION

Surprisingly, we found that the presence of cationic compounds, such as transfection reagents, do not inhibit transposase mediated integration of a transposon into a target nucleic acid. In fact, integration of a transposon into a target nucleic acid is actually enhanced by the presence of the cationic compounds. Furthermore, the frequency of self-integration was decreased. Enhancing transposition can mean increasing the kinetics of transposition, increasing the specificity of transposition into a target nucleic acid, or increasing the percentage single transposon integrations into a target nucleic acid.

Synaptic complexes were formed with transposase bound to transposon. Polycations were then added to the preformed integrator complexes, and a supercoiled target plasmid was added to the reaction in a solution in which the transposase is active. The integrator complexes inserted the transposon into the plasmid. In the presence of the enhancing reagent, insertion of transposon into the target nucleic acid is enhanced. In the absence of enhancing reagent, transposons are frequently integrated into other transposon nucleic acid. Also, in the absence of enhancing reagent, individual integrator complexes react with themselves, resulting in inversions and deletions of the transposon sequence. The presence of the enhancing reagent reduces the self-reactions and enhances single integrations into the target nucleic acid. We have tested the utility of a number of compositions for use as enhancing reagents, including: polycationic polymers polyethyleneimine and poly-L-lysine; cationic lipid mixtures TRANSIT®-INSECTA (1,2-dioleoyloxy-3-(trimethylammonio)-propane+dioleoyl-L-α-phosphatidylethanolamine+dilauroyl-phosphatidylethanolamine DLPE; Mirus) and LIPOFECTIN® (dioleoyl-L-α-phosphatidylethanolamine+N-[1-(2,3-dioleyloxy)propyl]-N,N,N-trimethylammonium chloride; Life Technologies); and cationic protein/cationic lipid mixture TRANSIT®-LT1 (histone+1,4-bis(3-oleoylamidopropyl) piperazine; Mirus). Other cationic compounds, especially those that bind to DNA (such as single stranded binding protein) or condense DNA may also be effective enhancing reagents.

A number of transfection reagents have been developed for delivery of DNA to cells. These reagents have generally not been shown to be effective for delivery of proteins to cells. We now show that the stability of the transposase-DNA interactions and integration competence of the complexes are maintained when associated with cationic transfection reagents. The transfection reagent is associated with the integrator complex in an appropriate buffer and incubated with the target nucleic acid.

Transposon integration systems require as little as two components: the transposase protein and a cognate transposon. The transposase may be purified from natural sources or it may be recombinant protein produced in vitro or it may be synthesized by methods known in the art. Recombinant transposase may be expressed in bacterial, yeast, insect or mammalian cells. The transposase may also be produced in cell-free expression systems. The transposase may have a wild-type amino acid sequence or it may have a modified amino acid sequence. Modifications include mutations that affect the activity or stability of the transposase or add functionality to the transposase. For example, mutations that enhance activity of the Tn5 transposase to produce a hyperactive protein are useful for the invention. Such mutations include the glutamate$_{54}$-to-lysine (EK54), methionine$_{56}$ to alanine (MA56), and leucine$_{372}$ to proline (LP372) mutations and combinations of these mutations (EK54,MA56, LP372 Tn5 transposase. SEQ ID 5).

For the purposes of this specification, a transposase means any protein that facilitates integration of a transposon into another nucleic acid. The term includes both transposases and integrases, which are used by viruses for integrating their genomes into host DNA. Integrases are also called recombinases or site-specific recombinases.

An integrator complex consists of a transposon and transposase in a synaptic complex. A synaptic complex is formed when transposase monomers bind to each of two specific end-binding sequences on the transposon and then associate to bring the proteins and the two ends of the transposon together. Preformed integrator complexes can be made from purified transposon and transposase in a wide variety of buffers provided the buffer allows the formation of synaptic complexes. Complexes may be made in buffers that contain or lack components in order to inhibit transposase activity until a target nucleic acid is added. For example, the Tn5 integration reaction, but not the formation of a synaptic complex, requires the presence of divalent cations [Goryshin et al. 2000]. Therefore, buffers lacking divalent cations, particularly magnesium, provide more stable formation of Tn5 synaptic complexes. Divalent cations can then be added at the same time as or after mixing of the Tn5 synaptic complex with target nucleic acid.

A transposon comprises any nucleic acid sequence that is flanked on both sides by repeat sequences to which a transposase can bind and form a synaptic complex. These sequences are called the end-binding sequences or elements and define the boundary of the transposon. The transposon is thus defined as the nucleic acid sequence containing the transposon elements together with all of the nucleic acid sequence between the elements. The transposon may exist as a linear nucleic acid molecule with the elements at the termini. Alternatively, the transposon may exist within a larger nucleic acid molecule such as a plasmid. Sequence outside the elements is separated from the transposon during the transposition process. The transposon is integrated into the target nucleic acid by the transposase. The Tn5 transposon comprises any nucleic acid sequence that is flanked on both sides by inverted repeat sequences to which Tn5 transposase can bind and form a synaptic complex. These sequences are called the end-binding sequences or Tn5 elements and define the boundary of the transposon. Tn5 elements are typically ~19 base pair sequences. Known elements include: outside elements, 5'-CTGACTCTTATA-CACAAGT-3' (SEQ ID 1); inside elements, 5'-CTGTCTCT-TGATCAGATCT-3' (SEQ ID 2); and the mosaic element, 5'-CTGTCTCTTATACACATCT-3' (SEQ ID 3).

The transposon may contain any nucleic acid sequence. The invention may be used to integrate therapeutic genes, siRNA genes, genes containing RNA polymerase III promoters (including the U6 or H1 promoter), modified U1 snRNA genes, reporter genes, marker or tag sequences, etc. More than one gene can be present on the transposon. For siRNA expression cassettes, the siRNA strands can either be transcribed as sense and anti-sense strands from separate promoters [Miyagishi and Taira 2002] or from a single promoter as a hairpin RNA that contains both sense and anti-sense [Sui et al. 2002]. The transposon may be used to integrate large DNA molecules, up to 10 kb or larger.

The term nucleic acid, or polynucleotide, is a term of art that refers to a polymer containing at least two nucleotides. Natural nucleotides contain a deoxyribose (DNA) or ribose (RNA) group, a phosphate group, and a base. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. Nucleotides are the monomeric units of nucleic acid polymers and are linked together through the phosphate groups. Polynucleotides with less than 120 monomeric units are often called oligonucleotides. The term polynucleotide includes deoxyribonucleic acid (DNA) and ribonucleic acid (RNA). Natural polynucleotides have a ribose-phosphate backbone. An artificial or synthetic polynucleotide is any polynucleotide that is chemically polymerized and contains the same or similar bases but may contain a backbone of a type other than the natural ribose-phosphate backbone. These backbones include, but are not limited to: PNAs (peptide nucleic acids), phosphorothioates, phosphorodiamidates, morpholinos, and other variants of the phosphate backbone of natural polynucleotides.

DNA may be in form of cDNA, synthetically polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, or derivatives of these groups.

The transposon may contain a marker sequence or an expression cassette coded to express a whole or partial protein, or RNA. Marker sequence comprises any sequence that can be detected such as by binding to proteins, coding for protein or RNA, or through nucleic acid hybridization techniques know in the art. An expression cassette refers to a natural or recombinantly or synthetically produced nucleic acid that is capable of expressing a gene(s). The term recombinant as used herein refers to a nucleic acid molecule that is comprised of segments of polynucleotide joined together by means of molecular biological techniques. The cassette contains the coding region of the gene of interest along with any other sequences that affect expression of the gene. A DNA expression cassette typically includes a promoter (allowing transcription initiation), and a sequence encoding one or more proteins. Optionally, the expression cassette may include, but is not limited to, transcriptional enhancers, non-coding sequences, splicing signals, transcription termination signals, and polyadenylation signals. The cassette may also code for an siRNA, modified U1 snRNA, antisense RNA or DNA, or a ribozyme. A siRNA is a nucleic acid that is a short, 15-50 base pairs and preferably 19-30 base pairs, double stranded ribonucleic acid. The siRNA consists of two annealed strands of RNA or a single strand of RNA that is present in a stem-loop. The siRNA contains sequence that is identical or nearly identical to a portion of a gene. RNA may be polymerized in vitro, recombinant RNA, contain chimeric sequences, or derivatives of these groups. An anti-sense polynucleotide is a polynucleotide that interferes with the function of DNA and/or RNA. Interference may result in suppression of expression. The polynucleotide can also be a sequence whose presence or expression in a cell alters the expression or function of cellular genes or RNA. A U1 snRNA gene can be modified to include up to 20 bases at the 5' end to target mRNA, thereby inhibiting expression of the target mRNA.

The term gene generally refers to a nucleic acid sequence that comprises coding sequences necessary for the production of a therapeutic nucleic acid (e.g., siRNA, modified U1 gene or ribozyme) or a therapeutic polypeptide or precursor. The polypeptide can be encoded by a full length coding sequence or by any portion of the coding sequence so long as the desired activity or functional properties (e.g., enzymatic activity, ligand binding, signal transduction, immune stimulation) of the full-length polypeptide or fragment are retained. The term encompasses the coding region of a gene. The term may also include sequences located adjacent to the coding region on both the 5' and 3' ends for a distance of about 1 kb or more. The sequences that are located 5' of the coding region and which are present on the mRNA are referred to as 5' untranslated sequences. The sequences that are located 3' or downstream of the coding region and which are present on the mRNA are referred to as 3' untranslated sequences. The term gene encompasses both cDNA and genomic forms of a gene. A genomic form or clone of a gene contains the coding region interrupted with non-coding sequences termed introns, intervening regions or intervening sequences. Introns are segments of a gene which are transcribed into nuclear RNA. Introns may contain regulatory elements such as enhancers. Introns are removed or spliced out from the nuclear or primary transcript; introns therefore are absent in the messenger RNA (mRNA) transcript. The mRNA functions during translation to specify the sequence or order of amino acids in a nascent polypeptide. The term non-coding sequences also refers to other regions of a gene including, but not limited to, promoters, enhancers, transcription factor binding sites, polyadenylation signals, internal ribosome entry sites, silencers, insulating sequences, matrix attachment regions. These sequences may be present close to the coding region of the gene (within 10,000 nucleotide) or at distant sites (more than 10,000 nucleotides). These non-coding sequences influence the level or rate of transcription and translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, and immunogenicity. One example of covalent modification of nucleic acid involves the action of LabelIT reagents (Mirus Corporation, Madison, Wis.).

A transfection reagent is a compound or compounds that bind(s) to or complex(es) with oligonucleotides and polynucleotides, and mediates their entry into cells. Examples of transfection reagents include, but are not limited to, cationic lipids and liposomes, polyamines, calcium phosphate precipitates, histone proteins, polyethyleneimine, and polylysine complexes. It has been shown that cationic proteins like histones and protamines, or synthetic cationic polymers like polylysine, polyarginine, polyornithine, DEAE dextran, polybrene, and polyethyleneimine may be effective intracellular delivery agents, while small polycations like spermine are ineffective. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via cell targeting signals that bind to receptors on or in the cell. For example, cationic liposomes or polylysine complexes have net positive charges that enable them to bind to DNA or RNA.

A polymer is a molecule built up by repetitive bonding together of two or more smaller units called monomers. Monomers can themselves be polymers. Polymers having fewer than 80 monomers are sometimes called oligomers. The polymer can be a homopolymer in which a single monomer is used or it can be copolymer in which two or more monomers are used. The polymer can be linear, branched network, star, comb, or ladder types of polymer. Types of copolymers include alternating, random, block and graft. The main chain of a polymer is composed of the atoms whose bonds are required for propagation of polymer length. For example in poly-L-lysine, the carbonyl carbon, $\alpha$-carbon, and $\alpha$-amine groups are required for the length of the polymer and are therefore main chain atoms. A side chain of a polymer is composed of the atoms whose bonds are not required for propagation of polymer length. For example in poly-L-lysine, the $\beta$, $\gamma$, $\delta$, and $\epsilon$-carbons, and $\epsilon$-nitrogen are not required for the propagation of the polymer and are therefore side chain atoms.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges.

Protein refers herein to a linear series of greater than 2 amino acid residues connected one to another via peptide bonds as in a polypeptide. Nucleic acid-binding proteins are proteins which have affinity for nucleic acid. The nucleic acid can be DNA or RNA and can be double-stranded or single-stranded. An example or a nucleic acid binding protein that binds to single stranded DNA is Single Strand Binding protein.

EXAMPLES

1) Formation of Transgene Constructs Containing Transposable Elements: Transposons were constructed in plasmid vectors. The DNA sequence located between the Tn5 elements plus the Tn5 elements themselves is the transposon. Tn5 elements can be the outer elements (ends), inner elements (ends), or mosaics of outer and inner elements. The mosaic elements (ME) are 19 bp inverted repeats that flank the DNA to be transposed (SEQ ID 1). Precisely at the end of the ME are PshA I restriction sites that allow the transposon DNA to be separated from the plasmid. Internal to the ME are suitable restriction sites that allow removal of the elements. Some examples of transposon constructs are shown in FIG. 1. All of the examples in FIG. 1 include the neomycin/kanamycin resistance gene with SV40 promoter and polyadenylation signal for expression in eukaryotic cells and the prokaryotic Tn5 promoter to drive expression in bacterial cells. Eukaryotic expression allows for selection of mammalian cells that have the integrated transposon. Prokaryotic expression allows for growth of the plasmid in bacterial cells. The origin of replication for bacterial amplification of the plasmids can be included in the transposon as in pNeo-Tn, pSEAP-Tn and pEGFP-Tn. Inclusion of the origin allows for plasmid rescue to determine the integration site in the mammalian genome. The origin can also be in the vector but outside of the transposon sequence, as in pNeo-siRNA-Tn. The vector sequence outside of the Tn5 ME is called the plasmid backbone. The backbone in pNeo-Tn, pSEAP-Tn and pEGFP-Tn is ~200 bp. The backbone of pNeo-siRNA-Tn is ~700 bp.

A) Transposon with mosaic element sequence elements: CTGTCTCTTATACACATCT-$(N)_x$-AGATGTG-TATAAGAGACAG The mosaic sequences are underlined (SEQ ID 3 and SEQ ID 4). SEQ ID 4 is the inverted repeat of SEQ ID 3. $(N)_x$ represents a sequence that is inserted between the flanking mosaic sequences.

B) Transposon Plasmid pNeo-Tn (FIG. 1)—Plasmid pNeo-Tn for transposition studies was constructed from plasmid pcDNA3 by insertion of the prokaryotic Tn5 promoter between the SV40 promoter and the neomycin/kanamycin resistance ($Neo^R$/$Kan^R$) gene, insertion of two Tn5 transposition mosaic elements (ME), and removal of the ampicillin gene, the CMV promoter, the bovine growth hormone poly A signal and the f1 ori. The Tn5 elements flank the sequences to be transposed and are inverted repeats. pNeo-Tn allows for selection with kanamycin in prokaryotic cells and with G418 in eukaryotic cells. pNeo-Tn as shown in FIG. 1 is also called pMIR117 and is 2,914 bp. pNeo-Tn without the Xba I site internal to one of the Tn5 elements is called pMIR3 and is 2,913 bp.

C) Transposon Plasmid pSEAP-Tn (FIG. 1)—The EcoR I/BstB I fragment of pMIR117, containing both mosaic elements and eukaryotic and prokaryotic promoters upstream of the neomycin/kanamicin$^R$ gene, was ligated to an EcoR I/BstB I fragment of pMIR7 containing the HSV thymidine kinase polyadenylation signal and an origin of replication. The resultant plasmid was pMIR123. An Sse8387 I restriction site was then inserted into pMIR123, resulting in pMIR124. An EcoR I/Sse8387 I fragment containing the human ubiquitin C promoter, 5' untranslated region and intron, SEAP cDNA, and SV40 polyadenylation signal from pMIR90 was then inserted into pMIR124, resulting in pMIR126. An internal PshA I site was removed by site-directed mutagenesis to result in pSEAP-Tn, also called pMIR136. pSEAP-Tn expresses human secreted alkaline phosphatase and it is 5,886 bp.

D) Transposon Plasmid pEGFP-Tn (FIG. 1)—Plasmid pEGFP-Tn has the cytomegalovirus (CMV) promoter driving expression of enhanced green fluorescent protein (EGFP); a bacterial origin of replication (ori); and the neomycin/kanamycin resistance gene with an SV40 promoter for expression in mammalian cells and a prokaryotic promoter for expression in bacterial cells. These sequences are flanked by the 19 bp mosaic Tn5 transposition elements. pEGFP-Tn was formed by inserting into the Ase I site of pEGFP-C1 (CLONTECH) a PCR fragment of plasmid pNeo-Tn5 containing the two Tn5 elements separated by a 232 bp backbone and flanked by restriction enzyme Ase I linkers. This plasmid is 5,077 bp.

E) Transposon Plasmid pNeo-siRNA-Tn (FIG. 1)—Plasmid pNeo-siRNA-Tn has the human U6 snRNA promoter for driving expression of siRNA. This plasmid is also called pMIR246. Restriction sites just downstream of the U6 promoter allow for a variety of siRNA sequences to be inserted into pMIR246. The siRNA sequence is determined by the desired target gene.

F) Transposon Plasmid pNeo-U1—Tn-The U6 siRNA expression cassette from pNeo-siRNA-Tn is replaced by two tandem U1 snRNA genes that each target the same mRNA to inhibit its expression.

2) Formation of Preformed Integrator Complexes: Plasmids pNeo-Tn (Example IB), pSEAP-Tn (Example 1C), and pEGFP-Tn (Example 1D) were purified with the QIAGEN Endo-free maxi-prep kit. Transposon DNA was released from the plasmid backbone by linearization with PshA I and the enzyme was removed by a QIAGEN QIAquick spin column.

Concentrations of DNA and transposase were varied to maximize formation of complexes containing one DNA molecule and two Tn5 transposase molecules while minimizing aggregation. Transposase-DNA complexes are preformed by incubating hyperactive mutant Tn5 transposase (53 kDa) in 1× Reaction Buffer (50 mM NaCl, 20 mM HEPES, pH 7.5) with PshA I linearized transposon DNA in a total volume of 20 µl as described in [Goryshin et al. 2000]. The transposase was used at a molar excess of 5- to 10-fold in a reaction volume sufficiently dilute to minimize formation of aggregates. Synaptic complexes were formed by incubation for 2 hours at 37° C. For delivery to mammalian cells, the complexes were concentrated and rinsed twice in a Microcon-100 microfiltration device, thereby replacing the reaction buffer with a physiological buffer and washing out most of the free transposase molecules. Samples of linear or supercoiled transposon DNA alone were prepared at the same DNA concentration. For the DNA sample without mosaic elements, but including transposase, the transposon plasmid was digested with restriction enzymes just internal to the Tn5 ME's. The large fragment was gel purified and added to Tn5 transposase in a mock reaction for complex formation. This mixture was rinsed and concentrated in Microcon-30's, however, because the uncomplexed transposase would filter through a Microcon-100.

Complexes were analyzed by agarose gel electrophoresis and ethidium bromide staining to determine how much of the DNA was complexed with transposase. Transposition complex formation with plasmid pNeo-Tn is shown in FIG.

Figure 3:
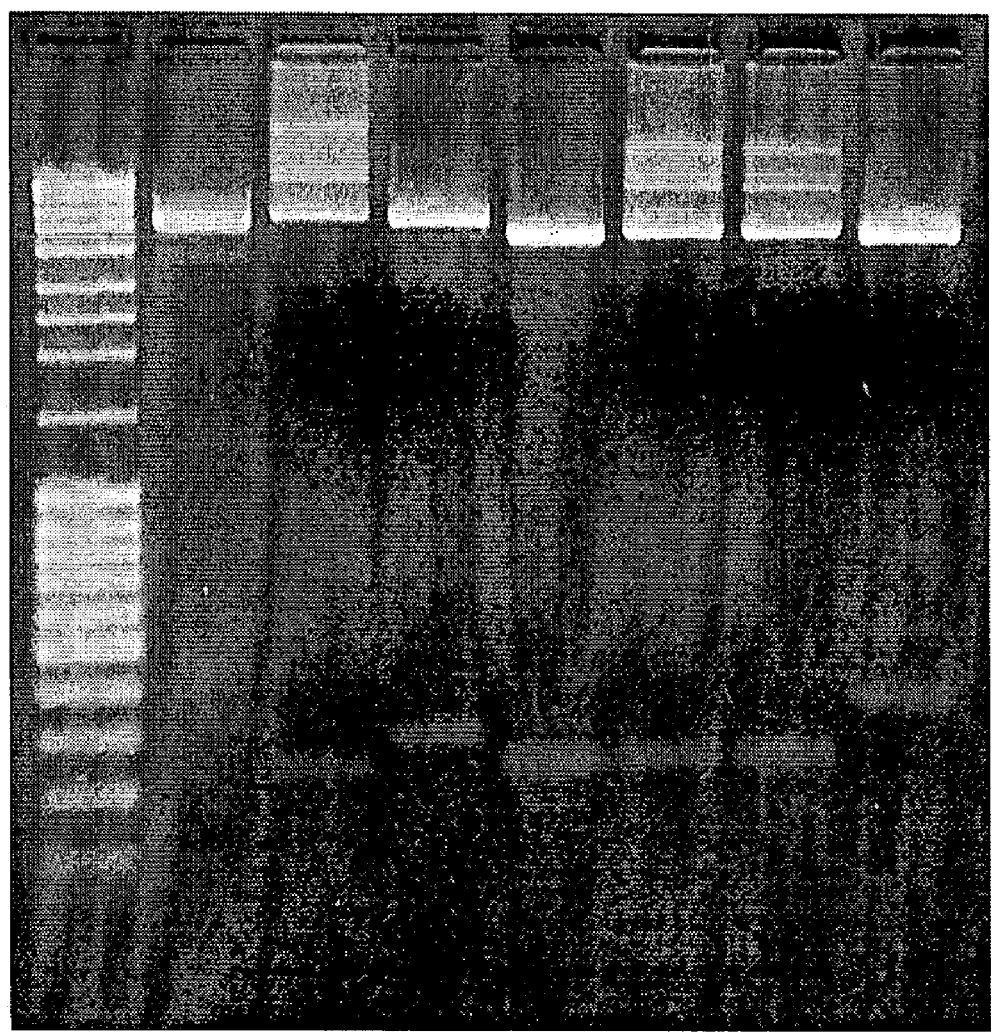
FIG. 3. Synaptic complexes formed with Neo-Tn and EGFP-Tn is dependent on the presence of mosaic elements. Lane 1: molecular weight markers. Lane 2: SEAP-TN with mosaic elements removed. Lane 3: SEAP-Tn/Tn5 transposase integrator complexes. Lane 4: SEAP-Tn with mosaic elements removed+Tn5 transposase, no integrator complexes formed. Lane 5: EGFP-Tn alone. Lane 6 and 7: EGFP-Tn/Tn5 transposase integrator complexes. Lane 8: EFGP-Tn with mosaic elements removed+Tn5 transposase, no integrator complexes formed. (TN DNA=SEAP-Tn or EGFP-Tn, ME=mosaic element, Tnp=Tn5 transposase)

2, lane 4. Transposition complex formation with pSEAP-Tn is shown in FIG. 3, lane 3. Transposition complex formation with pEGFP-Tn is shown in FIG. 3, lanes 6 and 7.

Figure 2:
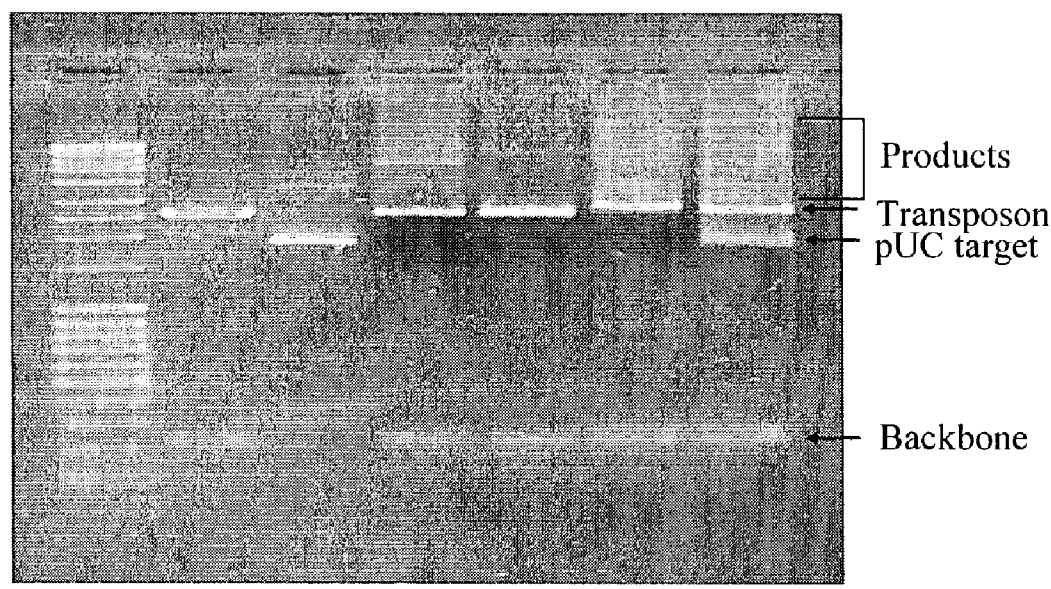
FIG. 2. Formation of Tn5 integrator complexes. Lane 1: MassRuler DNA Ladder Mix molecular weight markers (MBI Fermentas). Lane 2: Neo-Tn transposon+vector backbone fragment. pNeo-Tn is 2,913 bp. Lane 3: supercoiled target plasmid, pUC18. Lane 4: Tn5 transposase/Neo-Tn synaptic complexes. Lane 5: SDS dissociated synaptic complexes. Lane 6: integration products into Neo-Tn that form when magnesium is added to the synaptic complexes. Lane 7: integration products that result from addition of pUC18 to preformed synaptic complexes in the presence of magnesium. (TN DNA=Neo-Tn, TnP=Tn5 transposase)

3) Integration Reaction of Pre-formed Synaptic Complexes with Target DNA: Synaptic complexes were formed in 20 µl as in Example 2. 150 ng target DNA (pUC18) and 5 µl 5× Activity Assay Buffer (0.25 M NaCl, 0.125 M Tris HCl pH 7.5, 0.05 M $MgCl_2$, 0.01 M spermidine) were added to the preformed transposition complexes. The reaction was incubated at 37° C. for 30 min. To dissociate transposase from the DNA, 2 µl 5% SDS (0.3% final SDS conc.) was added to the reaction followed by heating at 68° C. for 5 min. Integration of the transposon into target DNA was monitored by agarose gel electrophoresis. The products are shown in FIG. 2, lane 7.

4) Integrator Complexes with Cationic Reagents: We utilized activity assays to evaluate the stability of hyperactive Tn5 transposase binding to linear or supercoiled transposon DNA. Integrator complexes of supercoiled or PshA I-linearized plasmid pNeo-Tn (FIG. 1) and the hyperactive Tn5 transposase were formed as described above and incubated with TRANSIT®-LT1, TRANSIT®-HELAMONSTER™, TRANSIT®-INSECTA, PLL, PEI, or LIPOFECTIN® transfection reagent in either PBS, Opti-MEM (Invitrogen) or complete media for 1-4 hours.
  A. TRANSIT® HELAMONSTER™ (Mirus Corporation): 0.6 µl HeLa reagent was added to the complexes. This mixture was incubated for 10 minutes at ambient temperature. Then 2 µl of a 10-fold dilution of MONSTER™ reagent was added.
  B. TRANSIT®-LT1 (Mirus Corporation): 0.6 µl reagent was added to the complexes and this mixture was incubated for 10 minutes at ambient temperature.
  C. TRANSIT®-INSECTA (Mirus Corporation): 0.8 µl reagent was added to the complexes and the mixture was incubated for 5 minutes at ambient temperature.
  D. LIPOFECTIN® (Life Technologies): 0.25 µl reagent was added to the complexes and the mixture was incubated for 15 minutes at ambient temperature.
  E. Poly-L-lysine: 0.4 µl of 1 mg/ml reagent was added to the complexes.
  F. Linear polyethyleneimine (PEI): 0.2 µl of 10 mg/ml reagent was added to the complexes.

An aliquot of each reaction was then transferred to transposase reaction buffer containing pUC18 as a target to determine transposase activity. 150 ng target DNA (pUC18) and 5 µl 5× Activity Assay Buffer were added. The reaction was incubated at 37° C. for 30 minutes. To dissociate transposase from the DNA, 2 µl 5% SDS was added to the reaction and then it was heated at 68° C. for 5 minutes prior to running on an agarose gel for analysis of integration products. Components of both TRANSIT®-HELAMONSTER™ and TRANSIT®-LT1 were not fully displaced by SDS treatment. To separate the nucleic acid components from proteins and other polycations, transposition reactions were phenol/chloroform extracted and ethanol precipitated. Reactions that included TRANSIT®-HELAMONSTER™, TRANSIT®-LT1 or PLL were treated with 4 µl 0.025% trypsin prior to phenol extraction.

Figure 4:
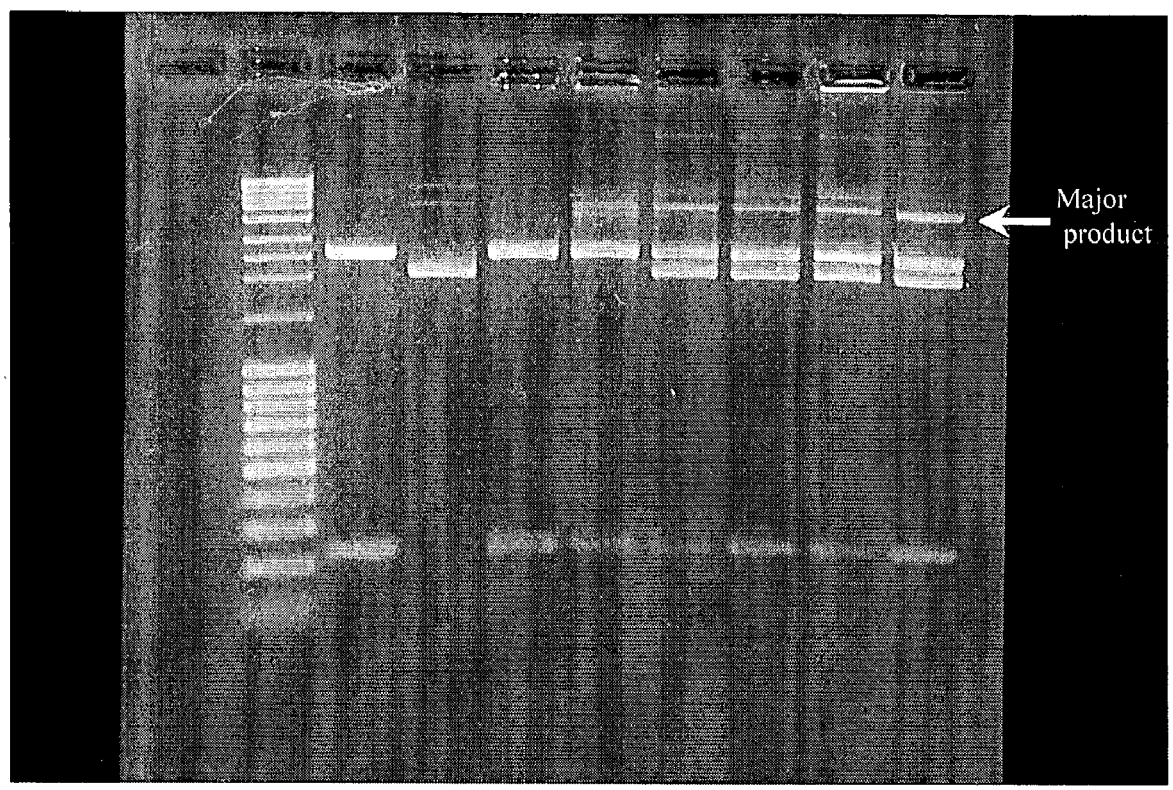
FIG. 4. Tn5 transposase is active in the presence of mammalian cell transfection reagents. Lane 1: molecular weight markers. Lane 2: Neo-Tn. Lane 3: supercoiled pUC18 target DNA. Lane 4: Neo-Tn+Tn5 transposase. Lane 5: Integration into Neo-Tn. Lane 6: Neo-Tn integration into pUC 18. Lane 7: Neo-Tn integration into pUC18 in presence of the transfection reagent Trans-IT LT1. Lane 8: Neo-Tn integration into pUC18 in presence of the transfection reagent Trans-IT Insecta. Lane 9: Neo-Tn integration into pUC18 in presence of the transfection reagent polyethyleneimine. (TN DNA=Neo-Tn, Tnp=Tn5 transposase, LT=TRANSIT®-LT1, In=TRANSIT®-INSECTA, PE=polyethyleneimine)

Recovered DNA samples from these reactions are shown in FIG. 4. Integration products are shown for Tn5 transposition in the absence of transfection reagent (FIG. 4, lane 6) as well as in the presence of LT1 (LT, FIG. 4, lane 7), Insecta (In, FIG. 4, lane 8) or PEI (PE, FIG. 4, lane 9). These results show that the transposase is active in the presence of cationic transfection reagents.

Figure 5:
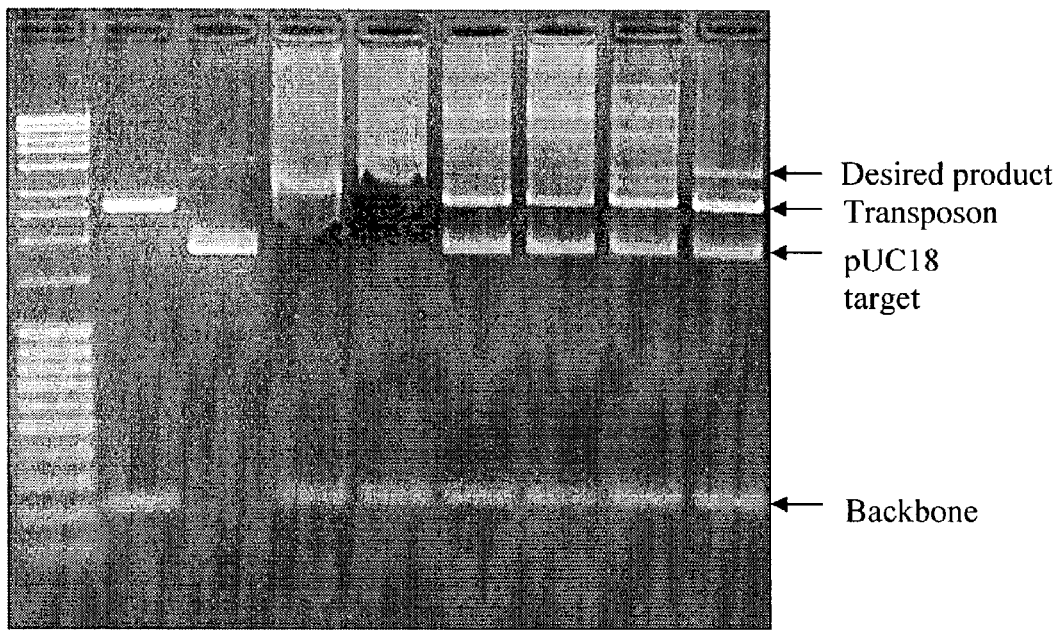
FIG. 5. The presence of polycations during the transposition reaction alters the target preference of the pre-formed synaptic complexes. Lane 1: molecular weight markers. Lane 2: Transposon (TN DNA), PshA I-linearized pMIR3. Lane 3: pUC18 target DNA. Lane 4: Transposon integration into pUC18 in the presence of TRANSIT®-HELAMONSTER™ (H). Lane 5: Transposon integration into pUC18 in the presence of TRANSIT®-LT1 (LT). Lane 6: Transposon integration into pUC18 in the presence of TRANSIT®-INSECTA (In). Lane 7: Transposon integration into pUC18 in the presence of LIPOFECTIN® (Lp). Lane 8: Transposon integration into pUC18 in the presence of poly-L-lysine (PL). Lane 9: Transposon integration into pUC18 in the presence of PEI (PE).

5) Integration Reaction of Transposition Complexes into Target DNA in the Presence of Polycations: Synaptic complexes were formed and treated with polycations as in Example 4 and 150 ng target DNA (pUC18) and 5 µl 5× Activity Assay Buffer were added. The reactions were incubated at 37° C. for 30 min. To dissociate transposase from the DNA, 2 µl 5% SDS was added to the reaction followed by heated at 68° C. for 5 min. Integration of transposons into the target DNA was monitored by agarose gel electrophoresis. The products are shown in FIG. 5, lanes 4-9. Components of both TRANSIT® HELAMONSTER™ and TRANSIT®-LT1 were not fully displaced by SDS treatment (FIG. 5, lanes 4 and 5). PEI treatment resulted in one major product that was the result of a single transposon integrating into the target plasmid (FIG. 5, lane 9). In the presence of PEI self integration of the transposon was reduced and single insertions into the target nucleic acid were enhanced.

6) Treatment of Transposition Complexes with PEI Results in More Productive Integration Events: Transposition reactions were prepared as in Example 4 using pMIR3 linearized with PshA I as the transposon DNA and pUC18 as the target plasmid. Transposition complexes were treated with LT1, Insecta, PEI, or left untreated. The cationic reagents were added to preformed integrator complexes prior to addition of magnesium. Control reactions, TN and TN+$Mg^{2+}$, did not contain the target plasmid. After the integration reaction, the nucleic acids from each reaction were phenol/chloroform extracted and ethanol precipitated as described in Example 4. Equal amounts of nucleic acid from each reaction were electroporated into DH10B E. coli and equal amounts of the cells were plated on LB-kanamycin/ampicillin plates. pMIR3 transposon encodes the kanamycin-resistance gene and pUC18 encodes ampicillin-resistance. An integration event between one transposon and one pUC18 plasmid results in a plasmid of approximately 6 kb that has both kanamycin and ampicillin resistance. Table 1 shows that there were 7 times more product plasmids from the PEI-treated transposition reaction than from the untreated reaction.

TABLE 1

Enhancement of Tn5 transposition by PEI

| Reaction Components | Number of Colonies |
| --- | --- |
| TN | 0 |
| TN + $Mg^{+2}$ | 0 |
| TN + pUC + $Mg^{+2}$ | 107 |
| TN + LT1 + pUC + $Mg^{+2}$ | 24 |
| TN + Insecta + pUC + $Mg^{+2}$ | 17 |
| TN + PEI + pUC + $Mg^{+2}$ | 718 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

REFERENCES

1. Blomer U, Naldini L, Kafri T, Trono D, Verma I M, Gage F H. Highly efficient and sustained gene transfer in adult neurons with a lentivirus vector. J Virol. 1997 September; 71(9):6641-6649.

2. Devine S E, Boeke J D. Efficient integration of artificial transposons into plasmid targets in vitro: a useful tool for DNA mapping, sequencing and genetic analysis. Nucleic Acids Res. 1994 Sep. 11;22(18):3765-3772.
3. Eichinger D J, Boeke J D. The DNA intermediate in yeast Ty1 element transposition copurifies with virus-like particles: cell-free Ty1 transposition. Cell. 1988 Sep. 23;54(7):955-966.
4. Goryshin I Y, Jendrisak J, Hoffman L M, Meis R, Reznikoff W S. Insertional transposon mutagenesis by electroporation of released Tn5 transposition complexes. Nat Biotechnol. 2000 January;18(1):97-100.
5. Goryshin I Y, Reznikoff W S. Tn5 in vitro transposition. J Biol Chem. 1998 Mar. 27;273(13):7367-7374.
6. Gwinn M L, Stellwagen A E, Craig N L, Tomb J F, Smith H O. In vitro Tn7 mutagenesis of *Haemophilus influenzae* Rd and characterization of the role of atpA in transformation. J Bacteriol. 1997 December;179(23):7315-7320.
7. Haapa S, Taira S, Heikkinen E, Savilahti H. An efficient and accurate integration of mini-Mu transposons in vitro: a general methodology for functional genetic analysis and molecular biology applications. Nucleic Acids Res. 1999 Jul. 1;27(13):2777-2784.
8. Ivics Z, Izsvak Z, Minter A, Hackett P B. Identification of functional domains and evolution of Tc1-like transposable elements. Proc Natl Acad Sci USA. 1996 May 14;93(10):5008-5013.
9. Ivics Z, Hackett P B, Plasterk R H, Izsvak Z. Molecular reconstruction of Sleeping Beauty, a Tc1-like transposon from fish, and its transposition in human cells. Cell 1997 Nov. 14;91(4):501-510.
10. Lampe D J, Churchill M E, Robertson H M. A purified mariner transposase is sufficient to mediate transposition in vitro. EMBO J. 1996 Oct. 1;15(19):5470-5479.
11. Miyagishi M, Taira K. U6 promoter-driven siRNAs with four uridine 3' overhangs efficiently suppress targeted gene expression in mammalian cells. Nat Biotechnol. 2002 May;20(5):497-500.
12. Reznikoff W S, Bhasin A, Davies D R, Goryshin I Y, Mahnke L A, Naumann T, Rayment I, Steiniger-White M, Twining S S. Tn5: A molecular window on transposition. Biochem Biophys Res Commun. 1999 Dec. 29;266(3):729-734.
13. Sui G, Soohoo C, Affar E B, Gay F, Shi Y, Forrester W C, Shi Y. A DNA vector-based RNAi technology to suppress gene expression in mammalian cells. PNAS 2002 99: 5515-5520.
14. Weinreich M D, Gasch A, Reznikoff W S. Evidence that the cis preference of the Tn5 transposase is caused by nonproductive multimerization. Genes Dev. 1994 Oct. 1;8(19):2363-2374.
15. York D, Welch K, Goryshin I Y, Reznikoff W S. Simple and efficient generation in vitro of nested deletions and inversions: Tn5 intramolecular transposition. Nucleic Acids Res. 1998 26(8):1927-1933.
16. Zhou M, Bhasin A, Reznikoff W S. Molecular genetic analysis of transposase-end DNA sequence recognition: cooperativity of three adjacent base-pairs in specific interaction with a mutant Tn5 transposase. J Mol Biol. 1998 Mar. 13;276(5):913-925.
17. Zhou M, Reznikoff W S. Tn5 transposase mutants that alter DNA binding specificity. J Mol Biol. 1997 Aug. 22;271(3):362-373.

We claim:

1. A process for enhancing transposase mediated integration of a transposon into a target nucleic acid outside a cell comprising:
   a) combining a transposase and the transposon in a solution to form a synaptic complex;
   b) combining said synaptic complex with a composition selected from the list consisting of: cationic polymers and cationic lipids; and,
   c) mixing the combined synaptic complex and composition of step (b) with the target nucleic acid outside a cell wherein transposition of the transposon into the target nucleic acid is enhanced.

2. The process of claim 1 wherein the transposase comprises Tn5 transposase.

3. The process of claim 2 wherein the Tn5 transposase comprises hyperactive Tn5 transposase.

4. The process of claim 3 wherein the hyperactive Tn5 transposase comprises the EK54MA56LP372 mutant Tn5 transposase (SEQ ID 5).

5. The process of claim 1 wherein the transposon comprises a Tn5 transposon.

6. The process of claim 1 wherein the cationic polymers consists of polyethyleneimines.

7. The process of claim 1 wherein the composition of step (b) consists of both cationic polymers and cationic lipids.

8. The process of claim 1 wherein the composition of step (b) is selected from the group consisting of poly-L-lysine (PLL) and poly-D-lysine.

9. A process for integrating a nucleic acid into a target nucleic acid comprising:
   a) making a transposon containing the nucleic acid;
   b) associating a transposase with the transposon to form a synaptic complex;
   c) combining the synaptic complex with one or more cationic polymers or cationic lipids or combination thereof in solution to form a composition; and,
   d) incubating the composition of step (c) with a target nucleic acid outside a cell, wherein the transposase integrates the transposon into the target nucleic acid.

* * * * *